United States Patent
Yoo et al.

(10) Patent No.: US 12,102,282 B2
(45) Date of Patent: Oct. 1, 2024

(54) SHOE MANAGEMENT APPARATUS

(71) Applicant: LG ELECTRONICS INC., Seoul (KR)

(72) Inventors: Hyunsun Yoo, Seoul (KR); Jeong Guen Choi, Seoul (KR); Joohyeon Oh, Seoul (KR); Jae Myung Lim, Seoul (KR); Byoungjoon Han, Seoul (KR); Sang Yoon Lee, Seoul (KR); Hyunju Kim, Seoul (KR); Jeaseok Seong, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 566 days.

(21) Appl. No.: 17/356,251

(22) Filed: Jun. 23, 2021

(65) Prior Publication Data
US 2021/0401264 A1  Dec. 30, 2021

(30) Foreign Application Priority Data

Jun. 24, 2020  (KR) .................. 10-2020-0077410
Jun. 24, 2020  (KR) .................. 10-2020-0077411
Jun. 24, 2020  (KR) .................. 10-2020-0077412
Jun. 24, 2020  (KR) .................. 10-2020-0077413
Jun. 24, 2020  (KR) .................. 10-2020-0077414
Jun. 24, 2020  (KR) .................. 10-2020-0077415
Jun. 24, 2020  (KR) .................. 10-2020-0077417
(Continued)

(51) Int. Cl.
*A47L 23/02* (2006.01)
*A47L 23/18* (2006.01)
(Continued)

(52) U.S. Cl.
CPC ............... *A47L 23/18* (2013.01); *A47L 23/02* (2013.01); *A61L 2/088* (2013.01); *A61L 2/10* (2013.01);
(Continued)

(58) Field of Classification Search
CPC ......... A47L 23/18; A47L 23/02; A47B 61/04; A61L 2/088; A61L 2/10; A61L 9/205
See application file for complete search history.

(56) References Cited

U.S. PATENT DOCUMENTS 5,179,790 A  1/1993 Poulos
6,880,711 B2  4/2005 Collier
(Continued)

FOREIGN PATENT DOCUMENTS

CN  102907914 A  2/2013
CN  109674436 A  4/2019
(Continued)

*Primary Examiner* — Sean E Conley
*Assistant Examiner* — Justin Hwang
(74) *Attorney, Agent, or Firm* — Birch, Stewart, Kolasch & Birch, LLP

(57) ABSTRACT

A shoe management apparatus including a cabinet defining an inner space for storing shoes, an exhaust port disposed at a rear surface of the inner space and discharging air into the inner space, and a circulation filter disposed on an inner wall of the cabinet and for filtering air within the inner space of the cabinet, the circulation filter including an upper portion including a first opening and a lower portion including a second opening, the lower portion being disposed below the upper portion.

20 Claims, 8 Drawing Sheets

(30) Foreign Application Priority Data

Dec. 8, 2020 (KR) .......... 10-2020-0170566
Mar. 9, 2021 (KR) .......... 10-2021-0031063

(51) Int. Cl.
*A61L 2/08* (2006.01)
*A61L 2/10* (2006.01)

(52) U.S. Cl.
CPC ..... *A61L 2202/122* (2013.01); *A61L 2202/26* (2013.01)

(56) References Cited

U.S. PATENT DOCUMENTS

| | | | |
|---|---|---|---|
| 2018/0015196 A1* | 1/2018 | Huang | A61L 2/088 |
| 2021/0071345 A1 | 3/2021 | Lee et al. | |
| 2021/0299311 A1 | 9/2021 | Yu | |

FOREIGN PATENT DOCUMENTS

| | | | | |
|---|---|---|---|---|
| CN | 112438681 A | | 3/2021 | |
| JP | 5-337002 A | | 12/1993 | |
| JP | 3023965 U | | 5/1996 | |
| JP | 2008-86419 A | | 4/2008 | |
| KP | 20-0357295 Y1 | | 7/2004 | |
| KR | 20-0291502 Y1 | | 10/2002 | |
| KR | 10-0407908 B1 | | 12/2003 | |
| KR | 20-0397164 Y1 | | 9/2005 | |
| KR | 10-0590794 B1 | | 6/2006 | |
| KR | 10-2008-0006908 A | | 1/2008 | |
| KR | 20-2011-0011197 U | | 12/2011 | |
| KR | 20110011197 U | * | 12/2011 | ............. A47B 61/04 |
| KR | 10-2015-0086056 A | | 7/2015 | |
| KR | 10-2019-0128460 A | | 11/2019 | |
| KR | 10-2020-0002725 A | | 1/2020 | |
| KR | 10-2020-0037035 A | | 4/2020 | |

* cited by examiner

[FIG. 1]
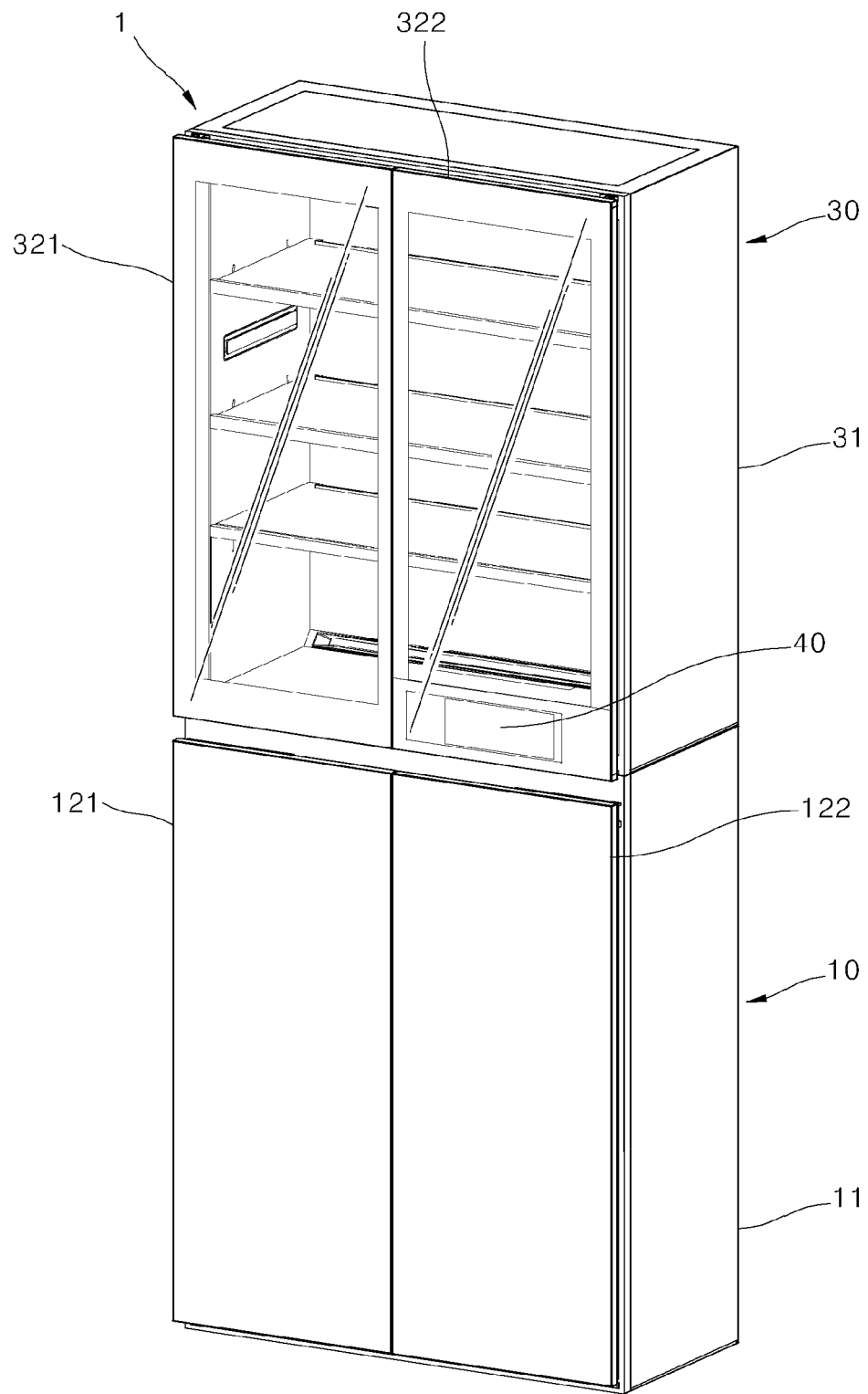

[FIG. 2]
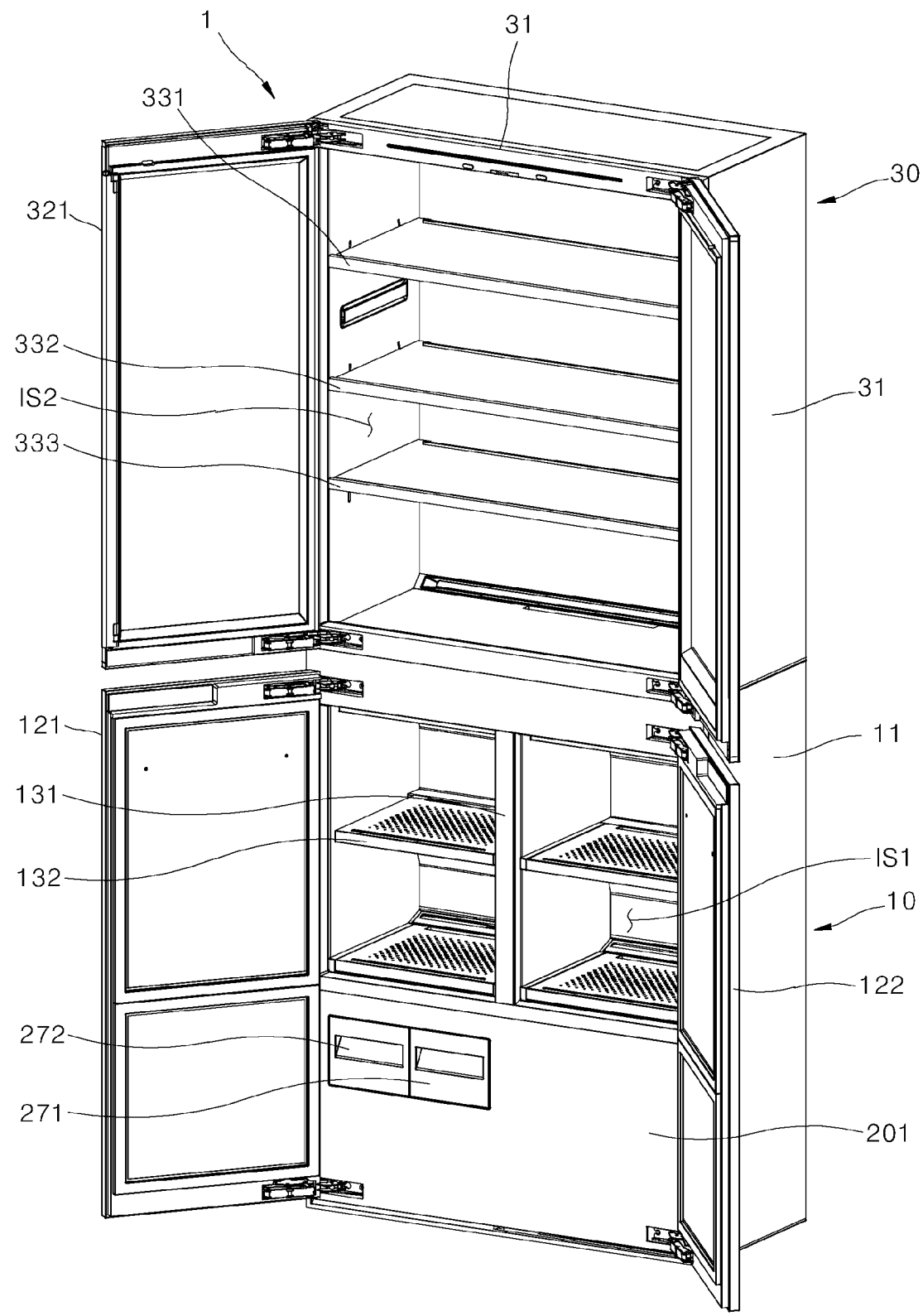

[FIG. 3]
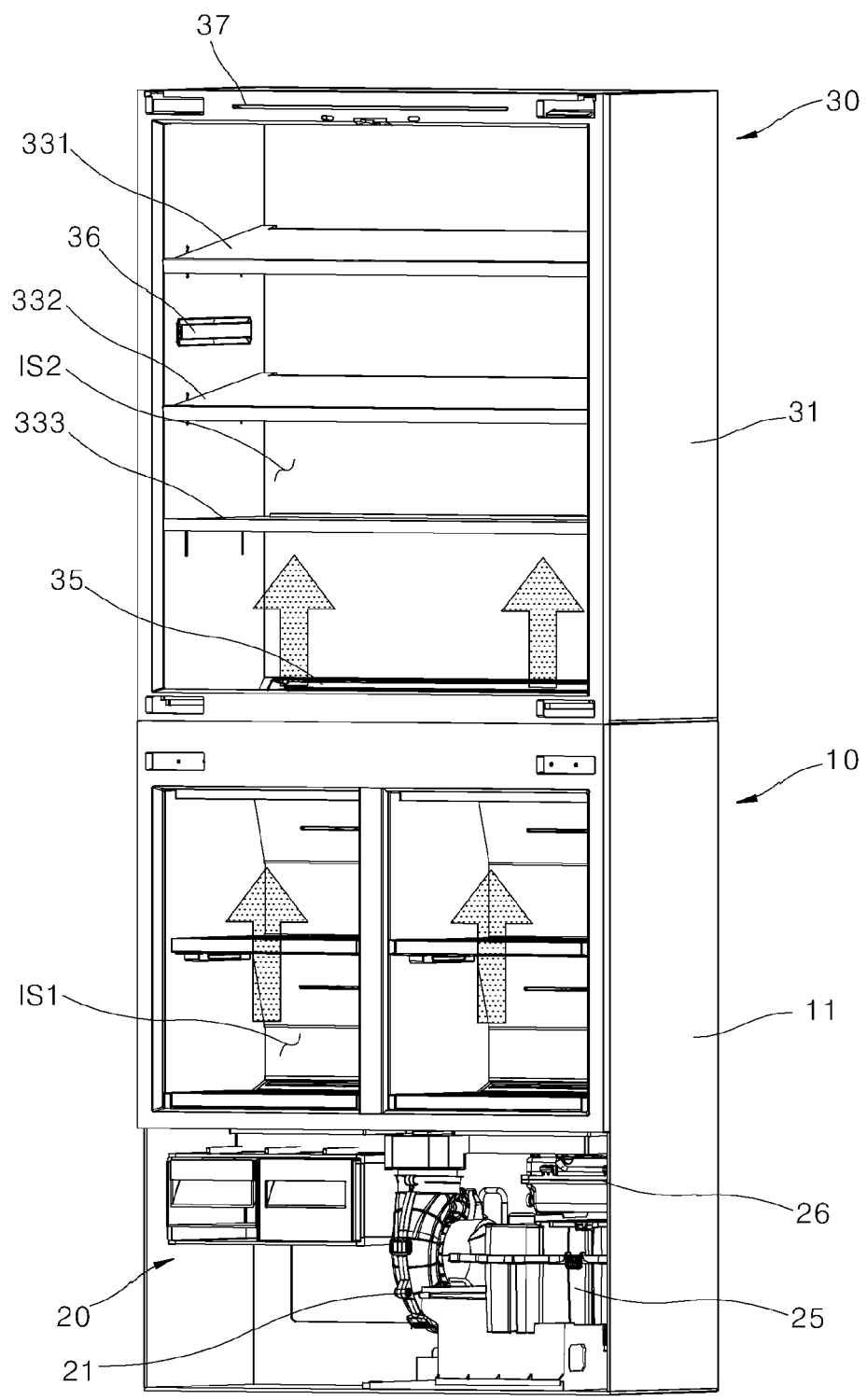

[FIG. 4]
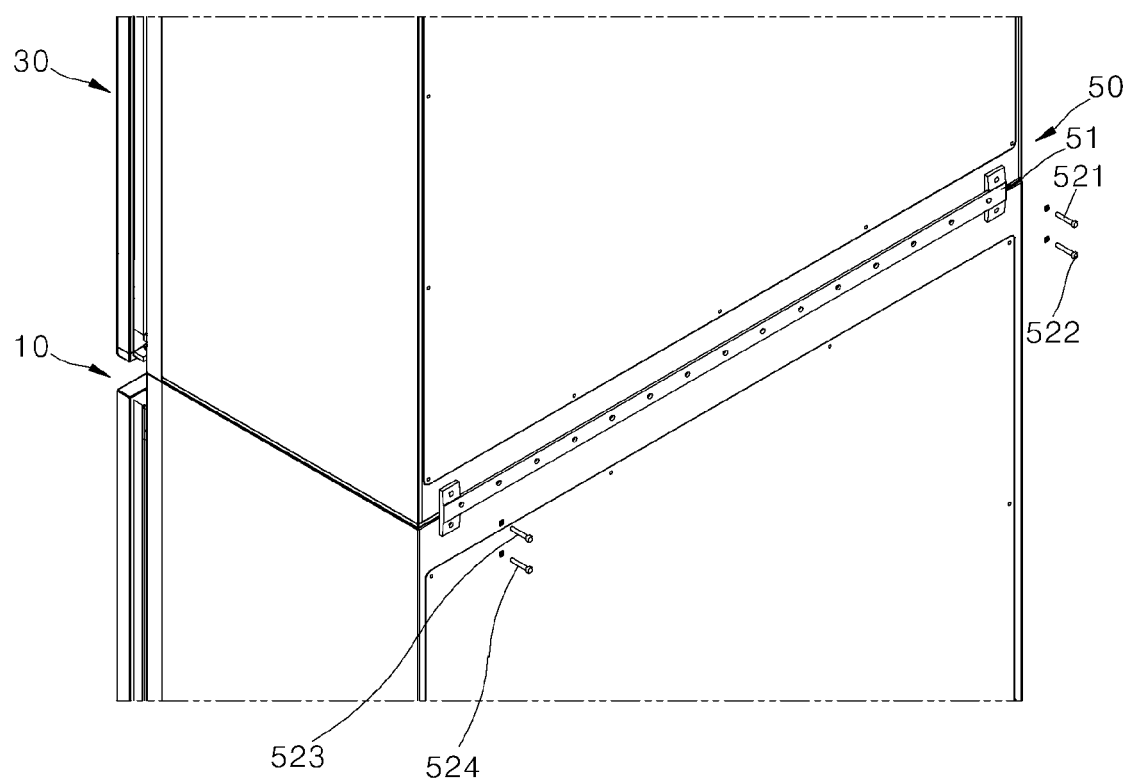

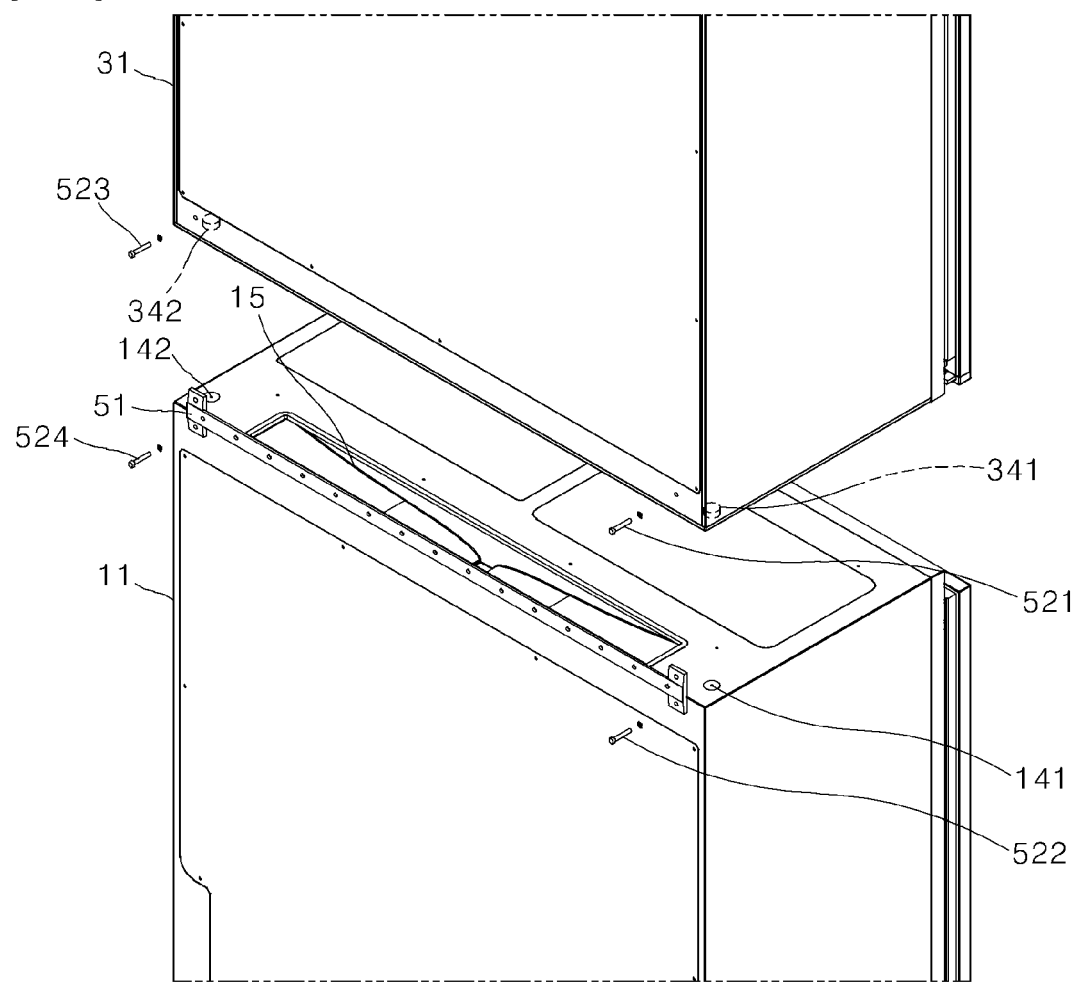
[FIG. 5]

[FIG. 6]
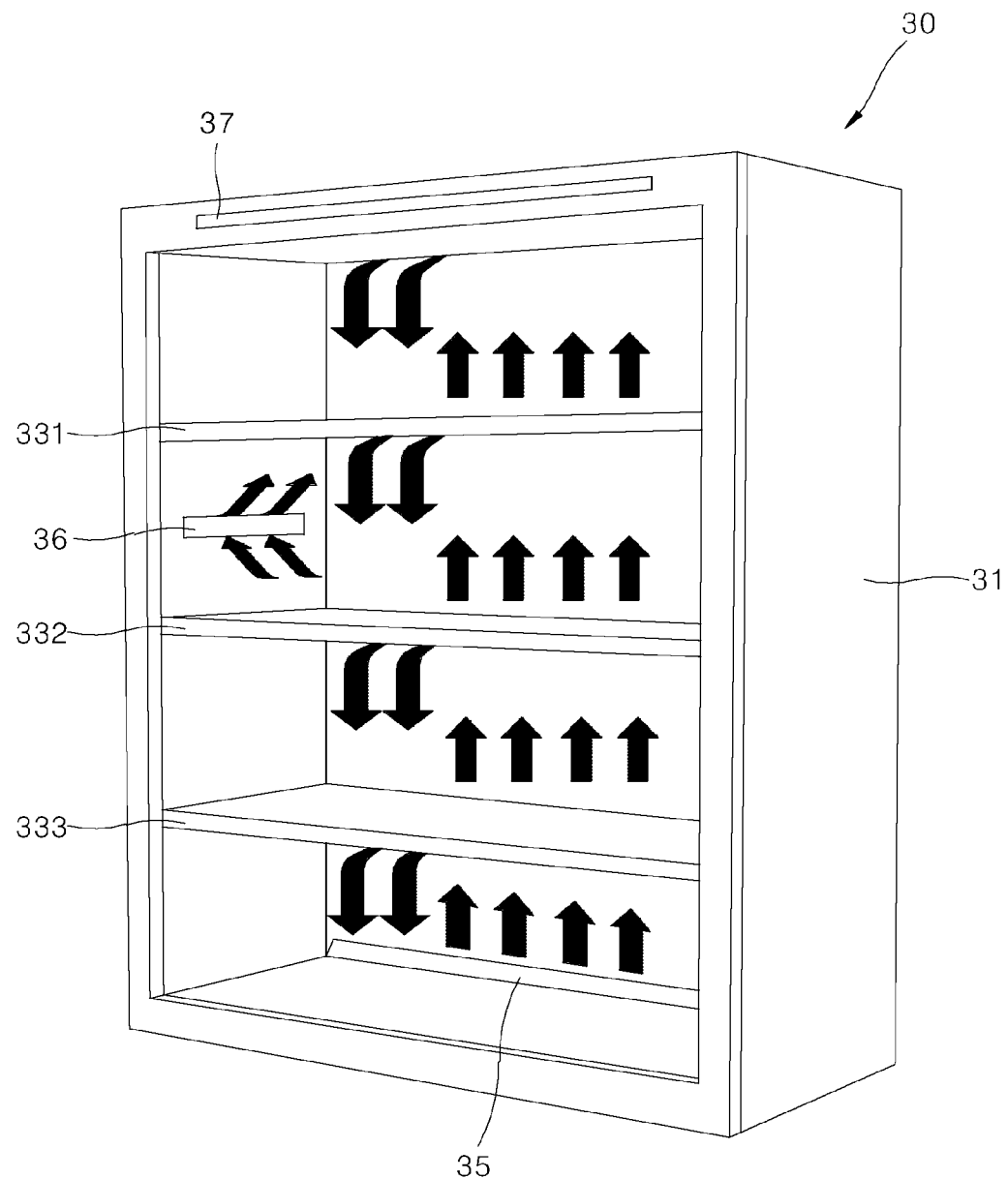

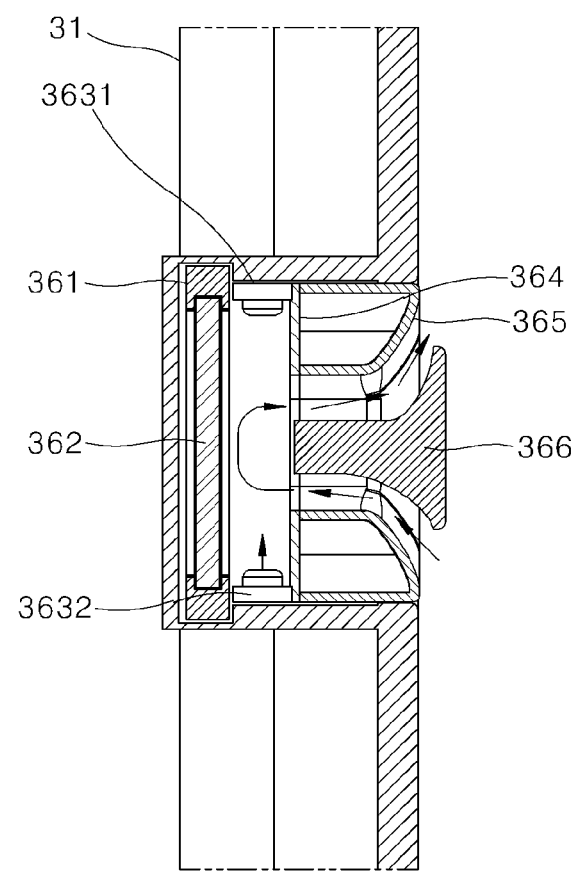

[FIG. 8]
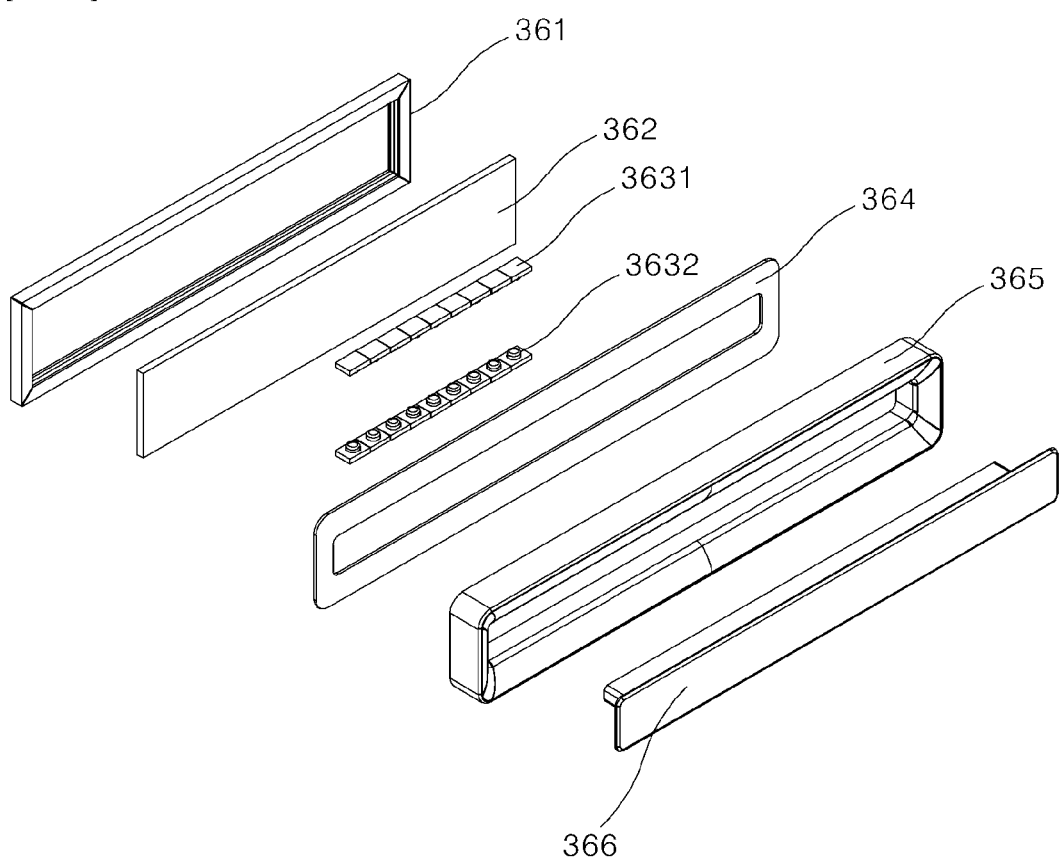

SHOE MANAGEMENT APPARATUS

CROSS-REFERENCE TO RELATED APPLICATIONS

This application claims priority to and the benefit of Korean Patent Application No. 10-2020-0077410, filed on Jun. 24, 2020, Korean Patent Application No. 10-2020-0077411, filed on Jun. 24, 2020, Korean Patent Application No. 10-2020-77412, filed on Jun. 24, 2020, Korean Patent Application No. 10-2020-0077413, filed on Jun. 24, 2020, Korean Patent Application No. 10-2020-77414, filed on Jun. 24, 2020, Korean Patent Application No. 10-2020-0077415, filed on Jun. 24, 2020, Korean Patent Application No. 10-2020-0077417, filed on Jun. 24, 2020, Korean Patent Application No. 10-2020-0170566, filed on Dec. 8, 2020, and Korean Patent Application No. 10-2021-0031063, filed on Mar. 9, 2021, the disclosures of which are incorporated herein by reference in their entirety into the present application.

BACKGROUND OF THE INVENTION

1. Field of the Invention

The present disclosure relates to a shoe management apparatus that can perform at least one function selected from among storage, sterilization, and decontamination of shoes.

2. Description of the Background Art

Generally, a shoe rack installed in an entrance room of a building is used to hold and organize various types of shoes.

However, when shoes wet with water or sweat are stored in a shoe rack, the humidity inside the shoe rack increases, causing deterioration and reduction in lifespan of all shoes stored therein. In particular, with increasing demand for high-end shoes in recent years, interest is growing for an apparatus that can properly manage and maintain shoes to extend lifespan of the shoes.

In addition, shoes are generally used for outdoor activities and thus can be easily contaminated with dust, bacteria, and viruses. Therefore, it is important from the viewpoint of hygiene for households to frequently perform sterilization or decontamination of shoes.

SUMMARY OF THE INVENTION

Embodiments of the present disclosure provide a shoe management apparatus that can prevent contamination of an inner space for storing shoes.

Embodiments of the present disclosure provide a shoe management apparatus that can more effectively remove contamination of an inner space for storing shoes.

The above and other objects and advantages of the present disclosure will become apparent from the detailed description of the following embodiments in conjunction with the accompanying drawings. In addition, it will be readily understood that the objects and advantages of the present disclosure can be realized by features set forth in the appended claims or combinations thereof.

In accordance with one aspect of the present disclosure, a shoe management apparatus includes a circulation filter disposed on an inner side wall of a cabinet defining an inner space for storing shoes.

In one embodiment, the circulation filter may be formed with an upper opening and a lower opening, wherein the upper opening may have a larger area than the lower opening.

In accordance with another aspect of the present disclosure, a shoe management apparatus includes: a cabinet defining an inner space for storing shoes; an exhaust port disposed at a rear bottom of the inner space and allowing air to be discharged into the inner space therethrough; and a circulation filter disposed on an inner side wall of the cabinet and having a first opening formed at an upper portion thereof and a second opening formed at a lower portion thereof.

In one embodiment, the first opening may have a larger area than the second opening.

In one embodiment, the circulation filter may include: a filter frame inserted into an inner surface of the cabinet; a photocatalytic filter secured to the filter frame; a light source unit disposed between the filter frame and the inner space; a duct-counterpart structure disposed between the light source unit and the inner space and provided in the form of a hollow rectangle-shaped panel; a circulation duct coupled to the duct-counterpart structure; and an airflow deflector decoration disposed at a center of the circulation duct and defining the first opening between an upper surface of the airflow deflector decoration and the circulation duct and the second opening between a lower surface of the airflow deflector decoration and the circulation duct.

In one embodiment, the circulation duct may have a horizontally symmetrical shape and the airflow deflector may have a horizontally asymmetrical shape.

In one embodiment, the shoe management apparatus may further include an electric compartment disposed under the inner space and delivering air to the exhaust port.

The shoe management apparatus according to the present disclosure can more effectively remove contamination of an inner space for storing shoes, thereby preventing contamination of the inner space for storing shoes.

The above and other effects of the present disclosure will become apparent from the following detailed description of the present disclosure.

BRIEF DESCRIPTION OF THE DRAWINGS

The present invention will become more fully understood from the detailed description given hereinbelow and the accompanying drawings which are given by way of illustration only, and thus are not limitative of the present invention, and wherein:

FIG. 1 is a perspective view of a shoe management apparatus according to one embodiment of the present disclosure.

FIG. 2 is a front view of the shoe management apparatus according to an embodiment of the present disclosure shown in FIG. 1, with doors opened.

FIG. 3 is a perspective view of the shoe management apparatus according to an embodiment of the present disclosure shown in FIG. 1, with the doors and an electric compartment front panel removed therefrom.

FIG. 4 is a partial view of a back surface of the shoe management apparatus according to an embodiment of the present disclosure shown in FIG. 1.

FIG. 5 is a partial view of the shoe management apparatus according to an embodiment of the present disclosure shown in FIG. 1, with a first management apparatus separated from a second management apparatus.

FIG. 6 is a perspective view of the second management apparatus of the shoe management apparatus according to an embodiment of the present disclosure shown in FIG. 1, with doors removed therefrom.

FIG. 7 is an enlarged sectional view of a circulation filter of the shoe management apparatus according to one embodiment of the present disclosure shown in FIG. 6.

FIG. 8 is an exploded perspective view of the circulation filter of FIG. 7.

DETAILED DESCRIPTION

Reference will now be made in detail to various embodiments, examples of which are illustrated in the accompanying drawings such that the present disclosure can be easily implemented by those skilled in the art. Description of known functions and constructions that may unnecessarily obscure the subject matter of the present disclosure will be omitted. Like components will be denoted by like reference numerals throughout the specification.

It will be understood that, although the terms "first," "second," and the like may be used herein to describe various elements and the like, these elements should not be limited by these terms. These terms are only used to distinguish one element from another element. Thus, a first element discussed below could be termed a second element, or vice versa, without departing from the scope of the present disclosure.

It will be understood that when a component is referred to as being disposed "at an upper (lower) portion of" or on (or "under") another component, it can be directly formed to adjoin an upper surface ("a lower surface") of the other component, or intervening component(s) may also be interposed therebetween.

In addition, when a certain component is referred to as being "connected to," "coupled to" or "joined to" another component, these components may be directly connected to, coupled to or joined to each other or through another component, or intervening component(s) may also be "interposed" therebetween.

As used herein, the singular forms, "a," "an," and "the" are intended to include the plural forms as well, unless the context clearly indicates otherwise. Moreover, the terms "comprises," "comprising," "includes," and/or "including," when used in this specification, should not be construed to mean that a process, method, article, or apparatus comprising a list of elements or steps necessarily comprises all the elements or all the steps. Thus, such a process, method, article, or apparatus may be free from some of the elements or the steps, or may further include one or more other elements or steps.

Hereinafter, a shoe management apparatus according to some exemplary embodiments of the present disclosure will be described.

FIG. 1 is a perspective view of a shoe management apparatus 1 according to one embodiment of the present disclosure. The shoe management apparatus 1 may include a first management apparatus 10 and a second management apparatus 30. The first management apparatus 10 may include a first cabinet 11, a 1st first door 121, and a 2nd first door 122, and the second management apparatus 30 may include a second cabinet 31, a 1st second door 321, and a 2nd second door 322. The shoe management apparatus 1 may further include a display unit 40.

The first management apparatus 10 may be disposed at a lower portion of the shoe management apparatus 1. The first management apparatus 10 may perform at least one operation selected from among removal of contaminants, such as dust, sterilization, deodorization, dehumidification, drying, and coating for shoes placed therein. Here, the sterilization operation may include at least one selected from among ultraviolet (UV) sterilization and steam sterilization. UV sterilization may be an operation of irradiating the shoes with short-wave UV rays having a wavelength of about 100 nm to 280 nm. Steam sterilization may be an operation of sterilizing the shoes using steam generated by heating water. The steam may be generated by heating water to 100° C. In addition, the generated steam may have a temperature of 40° C. to 50° C.

The first management apparatus 10 may be an apparatus that performs at least two of the aforementioned operations (that is, contaminant removal, sterilization, deodorization, dehumidification, drying, and coating) for a relatively short period of time in order to remove contamination of shoes placed therein. For example, the first management apparatus may sequentially perform removal of contaminants, such as dust, from surfaces of the shoes placed therein, sterilization and deodorization using the short-wave UV rays and a photocatalyst, sterilization using steam, dehumidification and drying, and coating for providing repellency to water for a predetermined period of time (for example, 40 minutes). That is, the first management apparatus 10 may be referred to as an "intensive care apparatus".

The first cabinet 11 of the first management apparatus 10 may define an exterior of the first management apparatus 10. The first cabinet 11 may be provided in the form of a cuboid open at a front thereof.

The 1st first door 121 and the 2nd first door 122 of the first management apparatus 10 may be disposed at the front of the first cabinet 11.

The second management apparatus 30 may be disposed on an upper surface of the first management apparatus 10 and may have a lower surface that directly contacts the upper surface of the first management apparatus 10. The second management apparatus 30 may perform at least one operation selected from among sterilization, ventilation, and humidity control of a space in which shoes are placed. Here, the sterilization operation may be performed using the short-wave ultraviolet rays described above or a photocatalytic filter.

The second management apparatus 30 may be an apparatus that constantly performs operations necessary for preventing deterioration of shoes stored therein. That is, the second management apparatus 30 may be referred to as a "constant management apparatus" or "light care apparatus."

The second cabinet 31 of the second management apparatus 30 may define an exterior of the second management apparatus 30. The second cabinet 31 may be provided in the form of a cuboid open at a front thereof.

The 1st second door 321 (that is, a first upper door) and the 2nd second door 322 of the second management apparatus may be disposed at the front of the second cabinet 31.

The display unit 40 may display a current operating state, abnormality, or the like of the shoe management apparatus 1. The display unit 40 may be disposed at a lower portion of the 2nd second door 322. The display unit 40 may be an electronic visual display, such as an LCD, TFT-LCD, OLED, a flexible display, and a three-dimensional display.

For convenience of description, a side or portion of the shoe management apparatus 1 at which the doors 121, 122, 321, 322 are disposed is defined as "front" and the other (i.e., opposite) side or portion of the shoe management apparatus 1 is defined as "rear".

FIG. 2 is a front view of the shoe management apparatus 1 according to an embodiment of the present disclosure shown in FIG. 1, with the doors opened.

The first management apparatus 10 may be formed at an upper portion thereof with a first inner space IS1 for storing shoes and may include an electric compartment 20 disposed under the first inner space IS1. An electric compartment front panel 201 may be disposed at a front of a space for the electric compartment 20. That is, the first cabinet 11 may define the first inner space IS1 and the space for the electric compartment 20, and the front of the electric compartment 20 may be covered by the electric compartment front panel 201.

The space for the electric compartment 20 may contain devices for dehumidifying air in the electric compartment 20, devices for discharging the dehumidified air to the first inner space IS1 and a second inner space IS2, a water supply container 271, and a drain container 272. The water supply container 271 may be detachably coupled to the first cabinet 11. The water supply container 271 may supply water to a steam generator 26 of the electric compartment 20.

The first management apparatus 10 may include at least one first partition 131 dividing the first inner space IS1 into multiple compartments. The first partition 131 may include a partition 131 dividing the first inner space IS1 from side to side.

As in this embodiment, the first inner space IS1 may be divided by a 1st first partition 131, a 2nd first partition 132, and a 3nd first partition 133. The 1st first partition 131 may divide the first inner space IS1 from side to side. The 1st first partition 131 may be disposed at a center of the first inner space IS1 with reference to the side-to-side direction. Each of the 2nd first partition 132 and the 3nd first partition 133 may divide the first inner space IS1 from top to bottom.

The second management apparatus 30 may be formed with a second inner space IS2 for storing shoes. That is, the second cabinet 31 may define the second inner space IS2 for storing shoes.

The second management apparatus 30 may include at least one second partition dividing the second inner space IS2 into multiple compartments. The second partition may include at least one partition dividing the second inner space IS2 from top to bottom.

As in this embodiment, the second inner space IS2 may be divided from top to bottom by a 1st second partition 331, a 2nd second partition 332, and a 3nd second partition 333.

FIG. 3 is a perspective view of the shoe management apparatus 1 according to an embodiment of the present disclosure shown in FIG. 1, with the doors 121, 122, 321, 322 and the electric compartment front panel 201 removed therefrom. In FIG. 3, arrows indicate air flow directions.

As described above, the electric compartment 20 is disposed at a lower portion of the first management apparatus 10. The electric compartment 20 may be formed separately from the first management apparatus 10 or may be formed integrally with the first management apparatus 10. Herein, the present disclosure will be described with reference to an example in which the electric compartment 20 is formed integrally with the first management apparatus 10.

The electric compartment 20 may force a fluid to flow in or out of the electric compartment. That is, the electric compartment 20 may supply the fluid to the first inner space IS1 and/or the second inner space IS2. Alternatively, the electric compartment 20 may draw in the fluid from the first inner space IS1 and/or the second inner space IS2. Here, the fluid may be air, steam, or a material containing substances necessary for management of shoes.

The electric compartment 20 may include a main fan 21 that draws in air, dehumidifies the drawn-in air, and discharges the dehumidified air. The electric compartment 20 may further include a housing 25 and a steam generator 26 that generates steam by heating water. The steam generator 26 may heat water to 100° C. The housing 25 may define a space for drying and/or heating air. The housing 25 may be formed on an upper surface thereof with an opening 251 through which air is introduced into the housing, may be formed therein with a space for accommodating a heat pump (more specifically, a condenser and/or an evaporator of the heat pump), and may be formed on a side surface thereof with an opening connected to the main fan 21 (specifically, a housing of the main fan).

The air discharged from the electric compartment 20 may be delivered to the first inner space IS1 of the first management apparatus 10 and/or the second inner space IS2 of the second management apparatus 30. To this end, the shoe management apparatus may be formed with a first fluid path communicating between the main fan 21 in the electric compartment 20 and the first inner space IS1 and a second fluid path communicating between the main fan 21 in the electric compartment 20 and the second inner space IS2.

The air inside the first inner space IS1 may be drawn back into the electric compartment. To this end, the shoe management apparatus may be formed with a return fluid path extending through the first inner space IS1 and the electric compartment 20.

The second management apparatus 30 may include a second exhaust port 35 through which the air delivered from the electric compartment 20 is discharged to the second inner space IS2. The second exhaust port 35 may be disposed at a rear bottom of the second inner space IS2 defined by the second cabinet 31, but the second exhaust port 35 may be disposed on any portion of a bottom surface of the second inner space IS2.

In addition, the second management apparatus 30 may include a circulation filter 36 removing harmful substances from the air inside the second inner space IS2. The circulation filter 36 may be disposed on an inner side surface of the second cabinet 31. Although one circulation filter 36 is shown in FIG. 3, it will be understood that the present disclosure is not limited thereto and the second management apparatus 30 may include multiple circulation filters 36. For example, another circulation filter may be disposed opposite the circulation filter 36 shown in FIG. 3.

In addition, the second management apparatus 30 may include a front discharge port 37 through which air in the second inner space IS2 is discharged to an outside of the shoe management apparatus. The front discharge port 37 may be disposed on an upper front surface of the second cabinet 31 or any outer surface of the second cabinet 31.

In addition, at least one of the partitions 331, 332, 333 of the second management apparatus 30 may be variable in angle with respect to a front-to-rear direction of the shoe management apparatus. That is, at least one of the partitions 331, 332, 333 of the second management apparatus 30 may be movable so as to be positioned at various different angles. When the multiple partitions are configured to be variable in angle with respect to the front-to-rear direction, each of the multiple partitions may be independently variable in angle with respect to the front-to-rear direction. With the configuration in which at least one of the partitions 331, 332, 333 is variable in angle with respect to the front-to-rear direction, the air in the second inner space IS2 can flow in various forms, thereby securing uniform ventilation throughout the second inner space IS2, including corners thereof.

As shown in FIG. 1, FIG. 2 and FIG. 3, the shoe management apparatus 1 according to an embodiment of the present disclosure may include: the first management apparatus including the electric compartment 20 and formed with the first inner space IS1 for storing shoes; and the second management apparatus 30 disposed on the upper surface of the first management apparatus 10 and formed with the second inner space IS2 for storing shoes. The electric compartment 20 may be disposed at the lower portion of the first management apparatus 10, and the first inner space IS1 may be formed on an upper side of the space for the electric compartment 20. The first management apparatus 10 may perform at least one operation selected from among contaminant removal, sterilization, deodorization, dehumidification, drying, and coating for shoes placed in the first inner space IS1 with relatively high intensity for a relatively short period of time (or any intensity level for any amount of time), and the second management apparatus 30 may perform at least one operation selected from among sterilization, ventilation, and dehumidification of the second inner space IS2 with relatively low intensity for a relatively long period of time (or with any intensity level for any amount of time), the intensity of the at least one operation of the second management apparatus 30 is less than the intensity of the at least one operation of the first management apparatus 10.

Here, "relatively high intensity" means that the temperature of the steam used in the sterilization operation is relatively high, the intensity of the UV rays used in the sterilization operation is relatively high, or the intensity of the airflow applied to shoes is relatively high.

As such, the shoe management apparatus according to this embodiment of the present disclosure can quickly remove contamination of shoes while allowing long-term storage of shoes without deterioration of the shoes. In addition, the shoe management apparatus according to this embodiment of the present disclosure can be built-in in an entrance room of a building due to structural compactness thereof.

In addition, according to this embodiment of the present disclosure, dehumidified air can be supplied to two management apparatuses using one electric compartment. Thus, it is possible to reduce the overall size of the shoe management apparatus.

FIG. 4 is a partial view of a back surface of the shoe management apparatus according to an embodiment of the present disclosure shown in FIG. 1. Referring to FIG. 4, the shoe management apparatus may include a longitudinal fastener 50 coupling the first management apparatus 10 to the second management apparatus 30. The longitudinal fastener 50 may include a longitudinal connection bar 51 and multiple longitudinal connection screws 521, 522, 523, 524.

Referring to FIG. 4, the shoe management apparatus according to an embodiment of the present disclosure may have a structure in which the first management apparatus 10 and the second management apparatus 30 are stacked vertically (i.e., in a vertical direction).

The longitudinal fastener 50 may couple the stacked first management apparatus 10 and second management apparatus 30 to each other. The longitudinal fastener 50 may be disposed on the back surface (i.e., rear surface) of the shoe management apparatus 1.

The longitudinal connection bar 51 may be disposed at a joint between the first management apparatus 10 and the second management apparatus 30 to be partially located on a back surface of the first management apparatus 10 and partially located on a back surface (i.e., rear surface) of the second management apparatus 30. The longitudinal connection bar 51 may have a horizontally elongated "H" shape, as viewed from behind the shoe management apparatus.

The longitudinal connection screws 521, 522, 523, 524 serve to securely couple the connection bar 51 to the first management apparatus 10 or the second management apparatus 30. Specifically, the longitudinal connection screws 521, 523 may couple the longitudinal connection bar 51 to the second management apparatus 30, and the longitudinal connection screws 522, 524 may couple the longitudinal connection bar 51 to the first management apparatus 10. When viewed from behind the shoe management apparatus, the longitudinal connection screws 521, 522 may be disposed on the right and the connection screws 523, 524 may be disposed on the left.

FIG. 5 is a partial view of the shoe management apparatus 1 according to an embodiment of the present disclosure shown in FIG. 1, with the first management apparatus 10 separated from the second management apparatus 30.

The first cabinet 11 of the first management apparatus 10 may include first signal contacts 141, 142 disposed on an upper surface thereof. In addition, the second cabinet 31 of the second management apparatus 30 may include second signal contacts 341, 342 disposed on a lower surface thereof.

Upon stacking the second management apparatus 30 on the upper surface of the first management apparatus 10, the first signal contacts 141, 142 may contact the second signal contacts 341, 342, respectively. The first management apparatus 10 may exchange necessary signals (data) with the second management apparatus 30 through signal transmission via the first signal contacts 141, 142 and the second signal contacts 341, 342. The signal transmission may be a wireless transmission, such as Bluetooth™, Zigbee™, Wi-Fi, etc.

In addition, the first management apparatus 10 may include a first exhaust port 15 disposed at an upper end thereof (i.e., the upper surface). Upon stacking the second management apparatus 30 on the upper surface of the first management apparatus 10, the first exhaust port 15 may be connected to the second exhaust port 35 of the second management apparatus 30. In this way, the air delivered from the electric compartment 20 can be discharged into the second inner space IS2 through the first exhaust port 15 of the first management apparatus 10 and through the second exhaust port 35 of the second management apparatus 30.

In one embodiment, the first management apparatus 10 may be used alone in the shoe management apparatus 1, unlike in the embodiments shown in FIG. 1 to FIG. 5. In this embodiment, the first exhaust port 15 may be used to dehumidify a space in which the shoe management apparatus 1 is installed (for example, an entrance room of a building).

FIG. 6 is a perspective view of the second management apparatus 30 of the shoe management apparatus 1 according to one embodiment of the present disclosure shown in FIG. 1, with the doors removed therefrom, and is provided to illustrate circulation of air in the second management apparatus 30. In FIG. 6, arrows indicate air flow routes.

The second exhaust port 35 may be disposed at a rear bottom edge of the second cabinet 31 of the second management apparatus 30. The second exhaust port 35 may be configured to discharge air upwards therethrough.

In addition, the second exhaust port 35 may have a horizontally elongated rectangular shape. That is, the second exhaust port 35 may be narrow in width and long in length. Accordingly, air can be discharged from the second exhaust port 35 in a narrow and long shape. In this way, the air discharged from the second exhaust port 35 can more easily flow to an upper end of the second inner space IS2 defined by the second cabinet 31.

In addition, as described above, at least one of the second partitions 331, 332, 333 may be variable in angle with reference to the front-rear direction. In this way, the flow of air in the second inner space IS2 can become more active and diverse.

The second cabinet 31 may include a circulation filter 36 disposed on an inner wall thereof. The circulation filter 36 may be configured to allow air to flow in from below and to flow out upwards. In one embodiment, the shoe management apparatus may further include a small fan disposed inside the circulation filter 36 to facilitate air circulation through the circulation filter 36.

The second cabinet 31 may include a front discharge port 37 formed on an upper front surface thereof. The front discharge port 37 is configured to discharge air from the second inner space IS2 to the outside of the shoe management apparatus 1 therethrough.

FIG. 7 is an enlarged sectional view of one embodiment of the circulation filter 36 of the shoe management apparatus 1 according to an embodiment of the present disclosure shown in FIG. 6, and FIG. 8 is an exploded perspective view of the circulation filter 36. The circulation filter 36 may include a filter frame 361, a photocatalytic filter 362, a first light source unit 363, a second light source unit 3632, a duct-counterpart structure 364, a circulation duct 365, and an airflow deflector decoration 366. In FIG. 7, arrows indicate air flow directions.

The filter frame 361 may be inserted into an inner side surface of the second cabinet 31. That is, the second cabinet 31 may have a groove formed on the inner side surface thereof to receive the filter frame 361 therein. That is, the filter frame 361 may be inserted into the groove of the second cabinet 31. The filter frame 361 may have a hollow rectangular shape and may serve to secure the photocatalytic filter 362 thereto.

The photocatalytic filter 362 may be inserted into the filter frame 361 to be secured to the filter frame 361. The photocatalytic filter 362 may be activated by light from the first light source unit 363 and the second light source unit to remove contaminants contacting a surface thereof.

The first light source unit 3631 and the second light source unit 3632 may be disposed between the filter frame 361 and the second inner space IS2. The first light source unit 3631 and the second light source unit 3632 may be disposed to face each other. As shown in the drawings, the first light source unit 3631 may be disposed adjacent to an upper section of the filter frame 361 to emit light downwards, and the second light source unit 3632 may be disposed adjacent to a lower section of the filter frame 361 to emit light upwards.

The duct-counterpart structure 364 may be provided in the form of a hollow rectangle-shaped panel. The duct-counterpart structure 364 may be disposed between the second inner space IS2 and the first and second light source units 3631, 3632.

The circulation duct 365 may define an exterior of the circulation filter 36. The circulation duct 365 may be coupled to the duct-counterpart structure 364. In addition, the circulation duct 365 may have a horizontally symmetrical shape.

When coupled to each other, the duct-counterpart structure 364 and the circulation duct 365 may define an exterior of an air flow path.

The airflow deflector decoration 366 may be disposed at a center of the circulation duct 365. Accordingly, an air flow path can be defined between an outer surface of the airflow deflector decoration 366 and an inner surface of the circulation duct 365.

The airflow deflector decoration 366 may have a horizontally asymmetrical shape. More specifically, the airflow deflector 366 may be formed such that an air flow path defined between an upper surface of the airflow deflector decoration 366 and the circulation duct 365 has a larger area than an air flow path defined between a lower surface of the airflow deflector 366 and the circulation duct 365.

That is, according to an embodiment of the present disclosure, the circulation filter 36 has an upper opening and a lower opening, as viewed from the front. Here, the upper opening may have a larger area than the lower opening. Due to this structure, the lower opening of the circulation filter 36 can serve as an air inlet and the upper opening of the circulation filter 36 can serve as an air outlet. In this way, the circulation filter 36 can more appropriately use the overall flow of air in the second inner space IS2 defined by the second cabinet 31, thereby more efficiently removing contamination from the second inner space IS2.

Although some exemplary embodiments have been described herein, it should be understood by those skilled in the art that these embodiments are given by way of example only, and that various modifications, variations, and alterations can be made without departing from the spirit and scope of the present disclosure. In addition, although advantageous effects provided by a certain configuration are not clearly described in description of the exemplary embodiments, it should be noted that expectable effects of the corresponding configuration should be acknowledged.

What is claimed is:

1. A shoe management apparatus, comprising:
a cabinet including an inner space for storing shoes;
an exhaust port disposed at a rear surface of the inner space and configured to discharge air into the inner space; and
a circulation filter disposed on an inner wall of the cabinet and configured to filter air within the inner space of the cabinet, the circulation filter including:
an upper portion including a first opening;
a lower portion including a second opening, the lower portion being disposed below the upper portion;
a duct-counterpart structure provided in a form of a hollow rectangle-shaped panel;
a circulation duct coupled to the duct-counterpart structure; and
an airflow deflector decoration disposed at a center of the circulation duct and defining the first opening between an upper surface of the airflow deflector decoration and the circulation duct and the second opening between a lower surface of the airflow deflector decoration and the circulation duct.

2. The shoe management apparatus according to claim 1, wherein the first opening has an area larger than an area of the second opening.

3. The shoe management apparatus according to claim 1, wherein the circulation filter further includes:
a filter frame disposed in an inner surface of the cabinet; and
a photocatalytic filter, and
wherein the photocatalytic filter is secured to the filter frame.

4. The shoe management apparatus according to claim 3, wherein the circulation filter further includes a light source assembly disposed between the filter frame and the inner space and configured to activate the photocatalytic filter.

5. The shoe management apparatus according to claim 4, wherein the light source assembly includes:
   a first light source unit including at least one light and configured to emit light downwards; and
   a second light source unit facing the first light source unit, including at least one light and configured to emit light upwards towards the first light source unit.

6. The shoe management apparatus according to claim 4, wherein
   the duct-counterpart structure is disposed between the light source assembly and the inner space.

7. The shoe management apparatus according to claim 6, wherein the circulation duct has a horizontally symmetrical shape and the airflow deflector decoration has a horizontally asymmetrical shape.

8. The shoe management apparatus according to claim 6, wherein the first opening is larger than the second opening.

9. The shoe management apparatus according to claim 1, further comprising an electric compartment disposed below the inner space, the electric compartment including a fan configured to deliver air to the exhaust port.

10. The shoe management apparatus according to claim 1, further comprising a front discharge port configured to discharge air from the inner space to outside of the shoe management apparatus.

11. The shoe management apparatus according to claim 10, wherein the exhaust port is configured to discharge the air upwards to the inner space, through the circulation filter and through the front discharge port.

12. The shoe management apparatus according to claim 1, wherein the cabinet further includes:
   a first partition;
   a second partition disposed below the first partition; and
   a third partition disposed below the second partition,
   wherein the circulation filter is disposed between the first partition and the second partition.

13. A shoe management apparatus, comprising:
   a cabinet including an inner space for storing shoes;
   an exhaust port disposed in the inner space and configured to discharge air into the inner space; and
   a circulation filter disposed on an inner wall of the cabinet and configured to filter air within the inner space of the cabinet, the circulation filter including:
      an upper portion including a first opening;
      a lower portion including a second opening, the lower portion being disposed below the upper portion;
      a photocatalytic filter;
      a light source assembly configured to activate the photocatalytic filter;
      a duct-counterpart structure disposed between the light source assembly and the inner space and provided in a form of a hollow rectangle-shaped panel;
      a circulation duct coupled to the duct-counterpart structure; and
      an airflow deflector decoration disposed at a center of the circulation duct and defining the first opening between an upper surface of the airflow deflector decoration and the circulation duct and the second opening between a lower surface of the airflow deflector decoration and the circulation duct.

14. The shoe management apparatus according to claim 13, wherein the first opening has an area larger than an area of the second opening.

15. The shoe management apparatus according to claim 13, wherein the circulation filter further includes a filter frame disposed in an inner surface of the cabinet,
   wherein the photocatalytic filter is secured to the filter frame, and
   wherein the light source assembly is disposed between the filter frame and the inner space.

16. The shoe management apparatus according to claim 13, wherein the light source assembly includes:
   a first light source unit including at least one light and configured to emit light downwards; and
   a second light source unit facing the first light source unit, including at least one light and configured to emit light upwards towards the first light source unit.

17. The shoe management apparatus according to claim 13, wherein the first opening is larger than the second opening.

18. The shoe management apparatus according to claim 13, further comprising an electric compartment disposed below the inner space, the electric compartment including a fan configured to deliver air to the exhaust port.

19. The shoe management apparatus according to claim 18, further comprising a front discharge port configured to discharge air from the inner space to outside of the shoe management apparatus,
   wherein the exhaust port is disposed at a rear surface of the inner space and is configured to discharge the air upwards to the inner space, through the circulation filter and through the front discharge port.

20. The shoe management apparatus according to claim 13, wherein the cabinet further includes:
   a first partition;
   a second partition disposed below the first partition; and
   a third partition disposed below the second partition,
   wherein the circulation filter is disposed between the first partition and the second partition.

* * * * *